United States Patent

Cooper et al.

Patent Number: 5,317,156
Date of Patent: May 31, 1994

[54] DIAGNOSTIC TESTS USING NEAR-INFRARED LASER ABSORPTION SPECTROSCOPY

[75] Inventors: David E. Cooper, Palo Alto; Clinton B. Carlisle; Haris Riris, both of Menlo Park, all of Calif.

[73] Assignee: SRI International, Menlo Park, Calif.

[21] Appl. No.: 827,209

[22] Filed: Jan. 29, 1992

[51] Int. Cl.$^5$ ............................................. G01N 21/35
[52] U.S. Cl. ............................ 250/345; 250/339.11; 250/346; 250/350; 250/351
[58] Field of Search ............... 250/345, 343, 339, 346, 250/350, 351

[56] References Cited

U.S. PATENT DOCUMENTS

| | | | |
|---|---|---|---|
| 3,805,074 | 4/1974 | McCormack | 250/343 |
| 4,594,511 | 6/1986 | Cooper et al. | 250/339 |
| 4,684,805 | 8/1987 | Lee et al. | 250/343 |
| 4,849,637 | 7/1989 | Cerff et al. | 250/343 |
| 4,937,448 | 6/1990 | Mantz et al. | 250/343 |
| 5,047,639 | 9/1991 | Wong | 250/343 |
| 5,146,294 | 9/1992 | Grisar et al. | 250/343 |

FOREIGN PATENT DOCUMENTS

| | | |
|---|---|---|
| 0263931 | 4/1988 | European Pat. Off. |
| 4012454 | 8/1991 | Fed. Rep. of Germany |
| 90/00732 | 1/1990 | PCT Int'l Appl. |
| 91/10895 | 7/1991 | PCT Int'l Appl. |

OTHER PUBLICATIONS

C. S. Irving et al., "Measurements of $^{13}CO_2/^{12}CO_2$ Abundance by Nondispersive Infrared Heterodyne Ratiometry as an Alternative to Gas Isotope Ratio Mass Spectrometry", *Analytical Chemistry*, Sep. 1986, vol. 58, No. 11, pp. 2172-2178.

P. S. Lee et al., "Tunable Diode Laser Spectroscopy for Isotope Analysis–Detection of Isotopic Carbon Monoxide in Exhaled Breath", *IEEE Transactions on Biomedical Engineering*, Oct. 1991, vol. 38, No. 10, pp. 966-973. Abstract of Japanese Patent Publication No. JP4042041, Published May 21, 1992, Abstract vol. 016218.

*Primary Examiner*—Carolyn E. Fields
*Attorney, Agent, or Firm*—David N. Slone

[57] ABSTRACT

RF modulation spectroscopy of a near infrared laser diode source is used to determine the amount of a target substance in a breath sample. In this type of modulation the laser output is modulated to produce sidebands displaced from the laser carrier by the modulation frequency. The modulated beam is passed through a gas sample which differentially absorbs the sidebands, the result of which is the conversion of some of the laser frequency modulation into amplitude modulation which is subsequently detected using a broadband photodetector. In certain tests, the target substance is a particular isotope, whose concentration is measured as an isotope ratio. In order to measure the presence of first and second isotopic species, provision is made to provide laser illumination at characteristic wavelengths for absorption lines for the first and second isotopic species of the gas. This may sometimes be accomplished using a single laser diode and scanning at least one of its operating parameters in order to achieve one of the wavelength difference. Alternatively, first and second laser diodes operating at the first and second wavelengths are used.

7 Claims, 10 Drawing Sheets

DIAGNOSTIC TESTS USING NEAR-INFRARED LASER ABSORPTION SPECTROSCOPY

BACKGROUND OF THE INVENTION

The present invention relates generally to medical diagnostic tests, and more specifically to metabolic breath tests utilizing isotope ratios.

Certain diagnostic medical tests rely on administering an isotopically labelled compound to a patient and then monitoring the patient's breath for metabolic products of the labelled compound. Traditional metabolic breath tests rely on administering a $^{14}$C-labelled substrate to a patient and then measuring the concentration of $^{14}$CO$_2$ exhaled on the breath. Since $^{14}$C is radioactive, it is easily detected with inexpensive radiation monitoring equipment. Unfortunately, this radioactivity is also a problem because of its health risk to the patient. One approach has been to replace the $^{14}$C isotope with a non-radioactive one, such as $^{13}$C. Although this eliminates the risks associated with exposure to $^{14}$C, it creates a new problem; how to detect $^{13}$CO$_2$ on the breath. This problem is further compounded by the fact that the relative natural abundance of $^{13}$C is approximately 1%, and considerable variability in this value is known to exist. Although a number of traditional approaches exist for monitoring $^{13}$C, including isotope-ratio mass spectrometry and nuclear magnetic resonance spectrometry, the associated instrumentation is exceedingly expensive and therefore limits the widespread use of $^{13}$C labelled compounds in diagnostic tests.

Lee and Majkowski (U.S. Pat. No. 4,684,805) consider the use of cryogenically cooled tunable infrared lead-salt laser diodes for this as well as other medical tests by monitoring certain molecular species on human breath. Since the strongest absorption lines of interest were in the 4-$\mu$m to 5-$\mu$m range, lead-salt laser diodes, which emit in the 3-$\mu$m to 30-$\mu$m region were a natural choice. However, lead-salt laser diodes and their associated detectors operate at liquid nitrogen temperatures. Furthermore, their output is generally multimode and is typically less than a milliwatt.

SUMMARY OF THE INVENTION

The present invention provides a number of simple, rapid, non-invasive diagnostic medical tests capable of screening patients for a number of diseases and metabolic disorders, to monitor their exposure to toxic and hazardous compounds, and to test for levels of certain drugs.

In brief, the present invention utilizes RF modulation spectroscopy of an infrared laser diode source to determine the amount of a target substance in a breath sample. In this type of frequency modulation the laser output is modulated to produce sidebands displaced from the laser carrier by the modulation frequency. The modulated beam is passed through a gas sample which differentially absorbs the sidebands, the result of which is the conversion of some of the laser frequency modulation into amplitude modulation which is subsequently detected using a broadband photodetector.

In certain tests, the target substance is a particular isotope, whose concentration is measured as an isotope ratio. In order to measure the presence of first and second isotopic species, provision is made to provide laser illumination at characteristic wavelengths for absorption lines for the first and second isotopic species of the gas. Depending on the separation of the two wavelengths, this may be accomplished using a single laser diode and scanning at least one of its operating parameters in order to achieve the wavelength difference. Alternatively, first and second laser diodes operating at the first and second wavelengths are used.

According to one aspect of the invention, absorption is measured in the near infrared. Although the strongest absorption lines for CO$_2$ are in the 4-$\mu$m to 5-$\mu$m region, there are a number of much weaker lines in the 1.6-$\mu$m region. Despite the fact that measurements of $^{12}$CO$_2$ absorption in the 1.6-$\mu$m region would normally be perceived as marginal at best, and measurements of $^{13}$CO$_2$ absorption would be perceived as impossible, we have found that some lines in this range can be measured with sufficient accuracy. This is particularly advantageous because excellent single-mode 1.6-$\mu$m laser diodes are commercially available. These devices are reliable and long-lived, and, more significantly, operate over a convenient range of temperature, say 0°–50° C. Thus, the techniques of the present invention can be implemented in relatively inexpensive portable instruments. In a specific embodiment, modulated infrared radiation is passed through a sample cell and a reference cell, and signals representing respective absorptions are correlated. In view of the weak absorption, a multi-pass cell design is preferred for the sample cell.

A further understanding of the nature and advantages of the present invention may be realized by reference to the remaining portions of the specification and drawings.

DESCRIPTION OF THE SPECIFIC EMBODIMENT(S)

Overview of Frequency Modulation Spectroscopy (FMS) and Wavelength Modulation Spectroscopy (WMS)

Two types of laser absorption spectroscopy, referred to as FMS and WMS, will be described. In laser absorption spectroscopy, a signal of interest results from the interaction of a probing field with a sample. This field is the laser beam, the wavelength of which is nearly resonant with an absorption line of the sample. By sinusoidally modulating the wavelength of the probing field, and simultaneously tuning the average wavelength of the field through the resonant feature of interest, a large signal appears that is proportional to the strength of the resonance.

FIGS. 1A–D illustrate schematically certain characteristics of different FMS regimes. FMS calls for the modulation of a laser at high frequencies (in the hundreds of MHz or GHz range), either by an external electrooptic modulator, or as in the case of laser diodes, by modulating the injection current. The modulated laser beam is passed through a sample, and the transmitted beam is demodulated using a fast photodetector and suitable processing electronics.

Figure 1A:
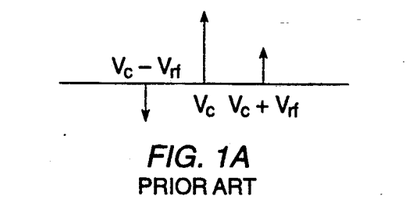
FIGS. 1A–F illustrate RF modulation techniques for use with the present invention.
Figure 1B:
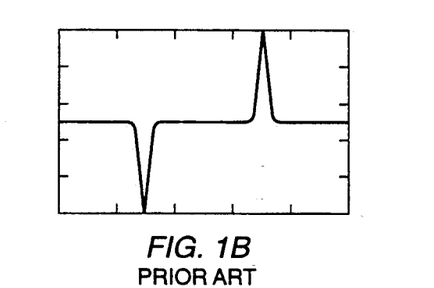

FIGS. 1A and 1B relate to what is known as single-tone FMS (STFMS), which uses a single modulation frequency. In frequency space, the modulated laser field consists of a carrier frequency, which is the natural emission frequency of the laser, and sidebands displaced from the carrier by integral multiples of the modulation frequency. In the weak modulation limit (frequency modulation index $\beta << 1$), the laser spectrum can be approximated by the first set of sidebands (FIG. 1A). For no absorption, the beat signal from the carrier and the upper sideband exactly cancels the beat signal from the carrier and the lower sideband because they have the same amplitude and are exactly 180° out of phase. When however, the laser is tuned over an absorption then the delicate balance between the beat signals is disturbed and a signal that resembles a first derivative of the absorption lineshape results (FIG. 1B). Although demodulation is usually performed at the modulation frequency, it can be performed at a harmonic of the modulation frequency.

STFMS offers advantages over direct absorption techniques. Direct absorption methods detect the signal as a change in the laser intensity and have their detection bandwidth in a region of the frequency spectrum where there is a large 1/f noise component. FMS detects the signal at the modulation frequency, where most lasers exhibit very little 1/f noise. Since the signal in FMS results from the differential absorption of the sidebands, for maximum sensitivity the modulation frequency should be comparable to the linewidth of the absorption. This means that for atmospherically broadened absorptions the modulation frequency should be in the 1-3 GHz range. This is a problem since detection at the modulation frequency means that a very high speed detector is required. Generally, infrared high-bandwidth detectors are not widely available, are very expensive, and have very small and damage-sensitive active areas, a fact that makes optical alignment rather cumbersome especially in the mid-IR region.

Figure 1C:
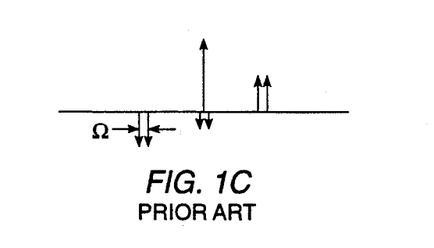
Figure 1D:
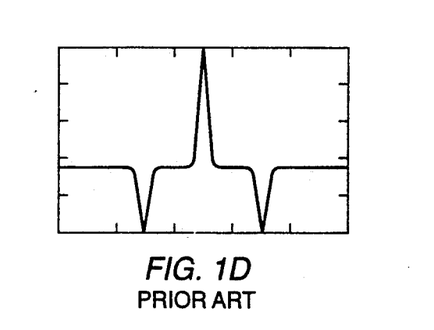

The need to reduce the detector bandwidth led to the development of two-tone FMS (TTFMS), which calls for the modulation of the laser at two high but closely spaced frequencies, $\nu_1$ and $\nu_2$ (FIG. 1C). TTFMS retains most of the basic characteristics of STFMS with the fundamental difference that the signal is now detected at the separation frequency $\nu_1 - \nu_2$ which can be on the order of a few MHz. The TTFMS signal depends on the frequency modulation index $\beta$, the amplitude modulation index M, and their phase difference $\psi$, and resembles the second derivative of the lineshape (FIG. 1D). For small absorptions the FM signal is linear with the size of the absorption. Demodulation can be performed at the difference of the modulation frequencies or at a harmonic of the difference.

Although the technique is in principle limited only by quantum or shot noise, in practice it is limited by several noise sources such as residual amplitude modulation (RAM), etalon fringes, laser excess or 1/f noise, and optical feedback, to which laser diodes are notoriously susceptible. Several schemes to reduce the effects of etalon fringes and subtract the RAM and laser excess noise have been implemented with considerable success. At the quantum noise limit for an FM system, the smallest absorption that can be detected is usually in the range of $10^{-7}$ to $10^{-8}$. Sensitivities at this level have been demonstrated with different laser systems. In practice, for a typical near-IR laser FM system and without any noise suppression scheme one can expect a sensitivity in the order of a few parts in $10^{-6}$.

Figure 1E:
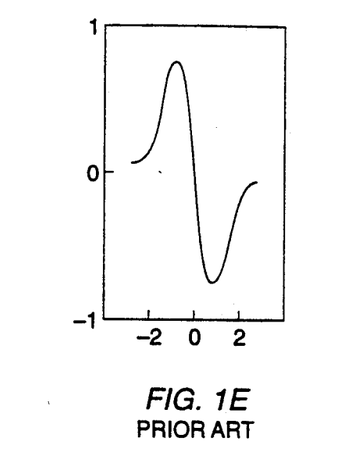
Figure 1F:
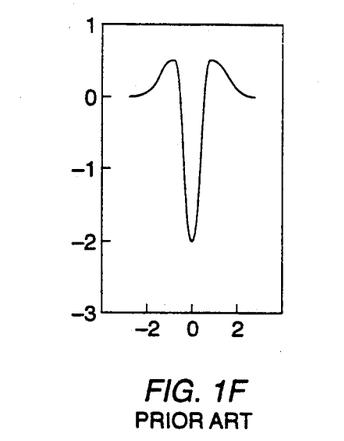

Wavelength modulation spectroscopy (WMS) predates the FMS techniques described above, and has been used with tunable diode laser sources since the late 1960s. It is an outgrowth of modulation techniques that were originally used to enhance the sensitivity of signals in nuclear magnetic resonance (NMR) and electron paramagnetic resonance (EPR) spectroscopy. These methods were in use during the 1950s in NMR and EPR. In NMR and EPR the probing field is an RF electromagnetic field that is nearly resonant with the nuclear or electron spins of the sample. In WMS (and FMS) this field is the laser beam, the wavelength of which is nearly resonant with an absorption line of the sample. In general one recovers signals from the resonance at all harmonics of the modulation frequency. Usually only the first and second harmonic signals are recorded, and they are proportional to the first and second derivatives of the resonant lineshape (FIGS. 1E and 1F).

In WMS, modulation frequencies in the kHz region have been traditionally used for sensitive spectroscopic detection. However, with the development of frequency modulation spectroscopy (FMS) in the 1980s, the advantages of modulation and detection in the MHz region have been appreciated, and WMS at MHz frequencies has been demonstrated. The differences between FMS and WMS are slight. In FMS, the modulation index of the laser is small, but the ratio of the modulation frequency to the width of the absorption feature is large. As a result, the absorption feature of interest is probed with a single isolated sideband or a small set of sidebands. In WMS the ratio of the modulation frequency to the width of the absorption feature is small, but the modulation index is large. As a result, the absorption feature is probed with a large number of sidebands. Thus, FMS and WMS may be viewed as limiting cases of a more general modulation spectroscopy.

Apparatus for Isotope Ratio Measurement

Figure 2:
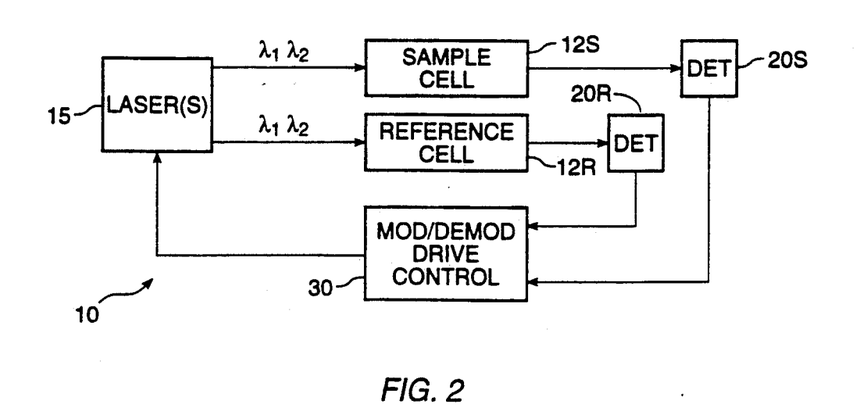
FIG. 2 is a high level optical schematic and block diagram of apparatus according to the invention.

FIG. 2 is a high level optical and electrical block diagram of apparatus 10 for measuring concentration of a target substance in a sample. A particular application of the present invention is the measurement of a target substance, typically present in trace amounts in a breath sample, and to that end, the apparatus includes a sample cell 12S and a reference cell 12R. In a particular application, the target substance is an isotopic species $^{13}CO_2$ which is measured relative to $^{12}CO_2$. A laser diode illumination subsystem 15 provides light at two wavelengths ($\lambda_1$ and $\lambda_2$) and directs a beam containing both wavelengths through each of the cells. The two wavelengths correspond to absorption lines for the two isotope species. As will be described below, the laser illumination subsystem may comprise a single laser diode or a pair of laser diodes, depending on the separation and the relative strengths of the absorption lines.

Associated with reference and sample cells 12R and 12S are detectors 20R and 20S for providing a signal representing the intensity of the light transmitted through the associated cell. Control circuitry 30 drives the laser(s), modulates the drive current according to a particular regime, tunes (scans) the laser wavelengths over the absorption lines, and demodulates the detector signals according to the particular regime. The modulation and demodulation circuitry will vary depending on the particular FMS regime.

Figure 3A:
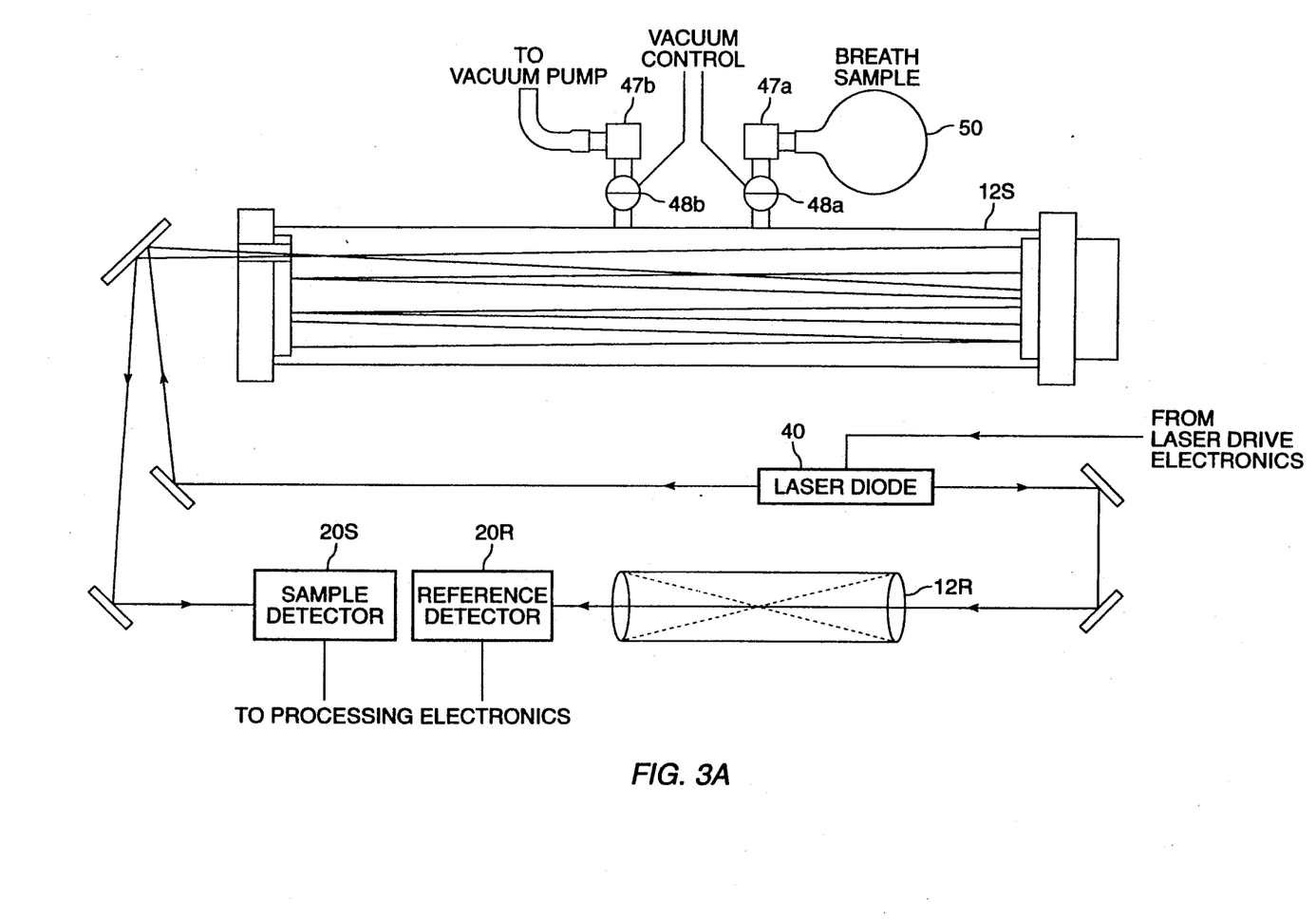
FIGS. 3A–B are schematics of laser illumination subassembly embodiments.

FIG. 3A is an optical schematic showing an embodiment where illumination subsystem 15 includes a single laser diode 40 that is capable of being tuned over a wavelength range that includes the first and second absorption lines. The front and rear facet outputs from the laser diode provide two beams, which are directed to the two cells. Alternatively, a single facet output could be directed to a beamsplitter to provide the two beams. In a preferred embodiment, the laser diode is a near-infrared laser diode, which is typically operated at temperatures in the 0°–50° C. range. This allows operation generally near room temperature, thereby avoiding the need for cryogenic cooling. Since the wavelength varies with temperature, the laser diode is preferably temperature controlled, as for example by being mounted on a thermoelectrically-controlled metal plate.

The reference cell contains a gas sample having a known, and preferably high, concentration of the target substance, and can thus be a single-pass cell. A representative reference sample is a 1:1 mixture of $^{12}CO_2$ and $^{13}CO_2$. The sample cell, on the other hand contains a sample having a small concentration of the target substance, and is thus preferably a multi-pass cell to keep the physical length within reason. In a particular embodiment, the cell is of the Herriot design and operates in the re-entrant mode. The sample cell is provided with entrance and exit gas ports 47a and 47b, which are controlled by respective vacuum-control solenoid valves 48a and 48b. A balloon or other receptacle 50 is used to collect a subject's breath sample and is then coupled to the entrance port.

Figure 3B:
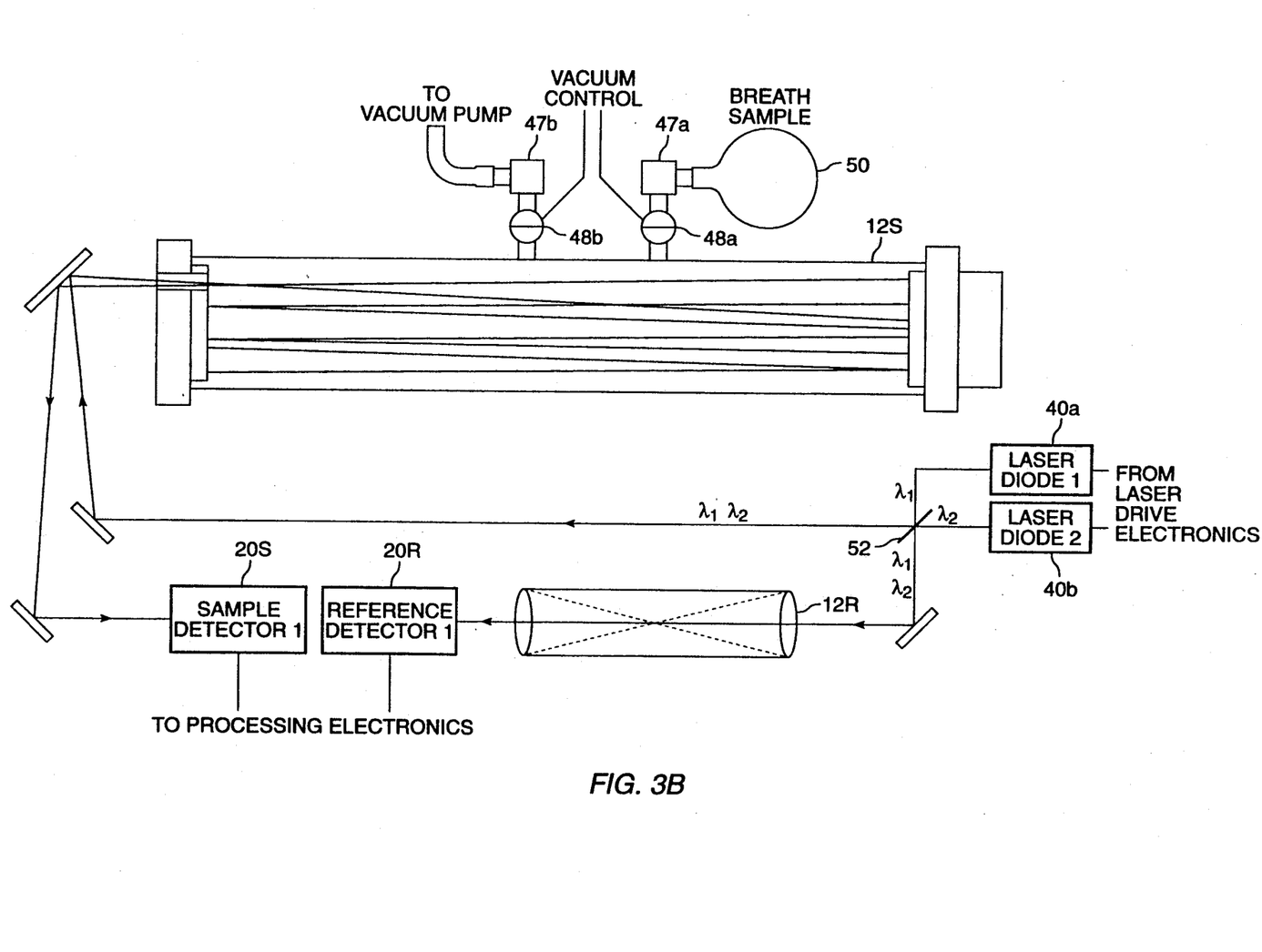

FIG. 3B is an optical schematic showing an embodiment where the illumination subsystem include first and second laser diodes 40a and 40b, operating at respective wavelengths corresponding to the two absorption lines. In this embodiment, both laser beams are directed to a beamsplitter 52, which operates to divide each beam into two components and to direct components at both wavelengths into each cell.

Figure 4A:
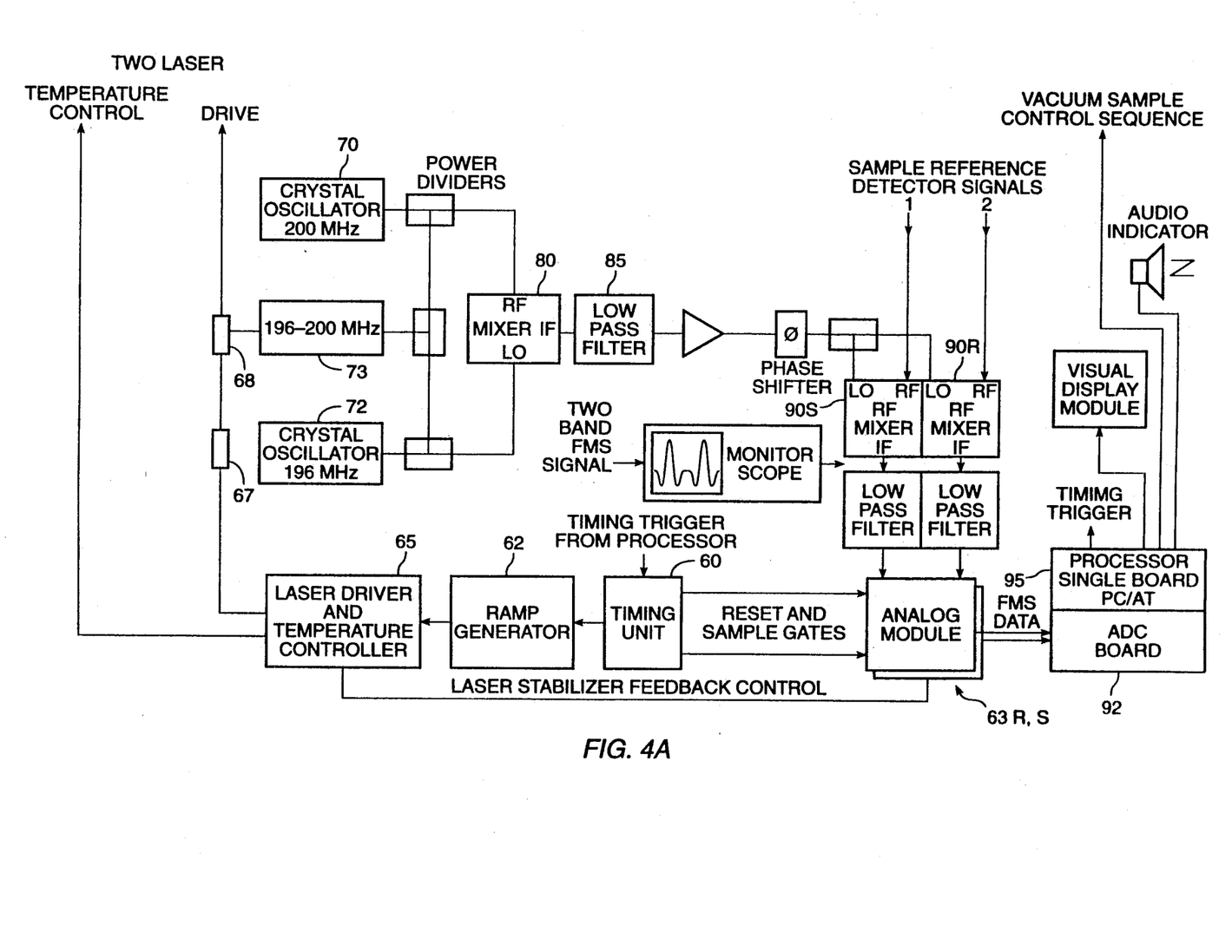
FIGS. 4A–B are block diagrams of two-tone frequency modulation/demodulation circuitry embodiments.

FIG. 4A is a block diagram of control circuitry for an embodiment using a single laser and TTFMS. In this embodiment, the single laser has its wavelength scanned over a range that includes the two absorption lines. The signal from a given detector is sampled during the respective intervals in which the wavelength of the laser is being scanned over the respective absorption lines. A timing unit 60, under microprocessor control, provides signals for sequencing a test procedure. To this end, it controls a ramp generator 62 and provides reset and sample gate signals to analog data modules 63R and 63S. The ramp generator provides a signal to laser drive circuitry 65 to control the wavelength scanning. The laser drive current is passed through a low-pass filter 67 and an RF bias network 68. Analog modules 63R and 63S receive demodulated signals from detectors 20R and 20S A pair of crystal oscillators 70 and 72 provide signals at the two modulation frequencies; 196 MHz and 200 MHz are representative. Each of the signals is split, and respective first portions of the signals are combined and passed through a band-pass filter 73 to RF bias network 68. The other portions of the oscillator signals are applied to the RF and LO inputs of a mixer 80, the IF output signal from which is passed through a low-pass filter 85 to generate a signal at the difference of the two frequencies (4 MHz in this case). The difference signal is applied to the LO inputs of a pair of mixers 90R and 90S, which receive the detector signals at their respective RF inputs, and provide the demodulated signals at their respective IF outputs. These signals are low-pass filtered and communicated to analog modules 63R and 63S. The analog signals are communicated to analog-to-digital (A/D) conversion circuitry 92, and the digitized values are sent to a computer 95 for processing.

Figure 4B:
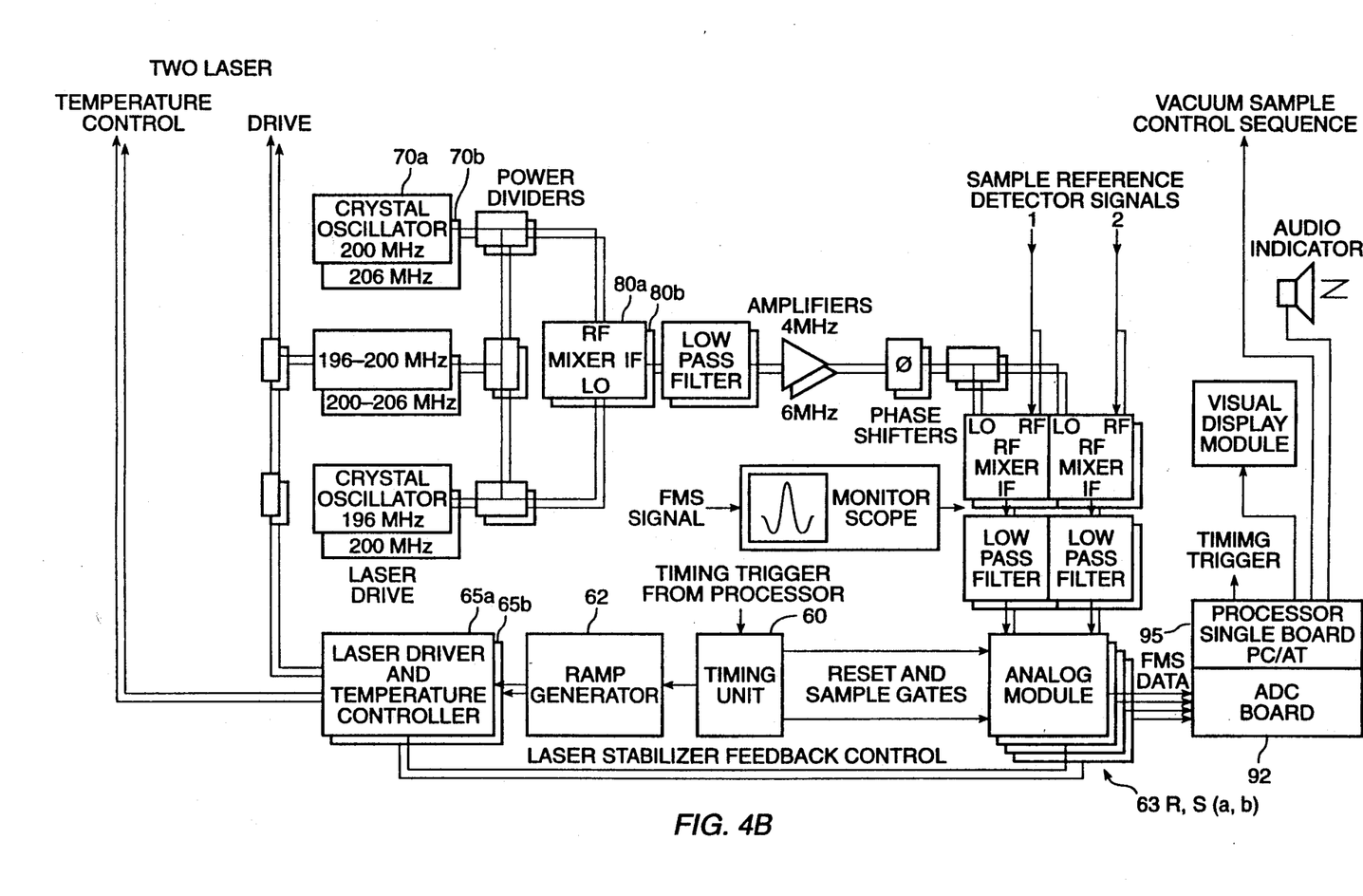

FIG. 4B is a block diagram of control circuitry for an embodiment using two lasers and TTFMS. Reference numerals corresponding to those in FIG. 4A are used, but with the suffixes a and b corresponding to the circuit elements for laser diodes 40a and 40b. In this embodiment, each laser has its wavelength scanned over a range that includes a single one of the two absorption lines. In this embodiment, each laser is modulated at a pair of frequencies, but the difference of the two frequencies for one laser is different from that for the other. For example, the first laser may be modulated at 196 MHz and 200 MHz (corresponding to the embodiment of FIG. 4A) while the second laser may be modulated at 200 MHz and 206 MHz. Thus each detector provides signals corresponding to the two sets of modulation frequencies. The circuitry is basically similar to that of the single laser embodiment, except that the modulation, demodulation, and laser driver circuits are duplicated so that each detector signal is demodulated at 4 MHz and 6 MHz (for the specific example).

Figure 5A:
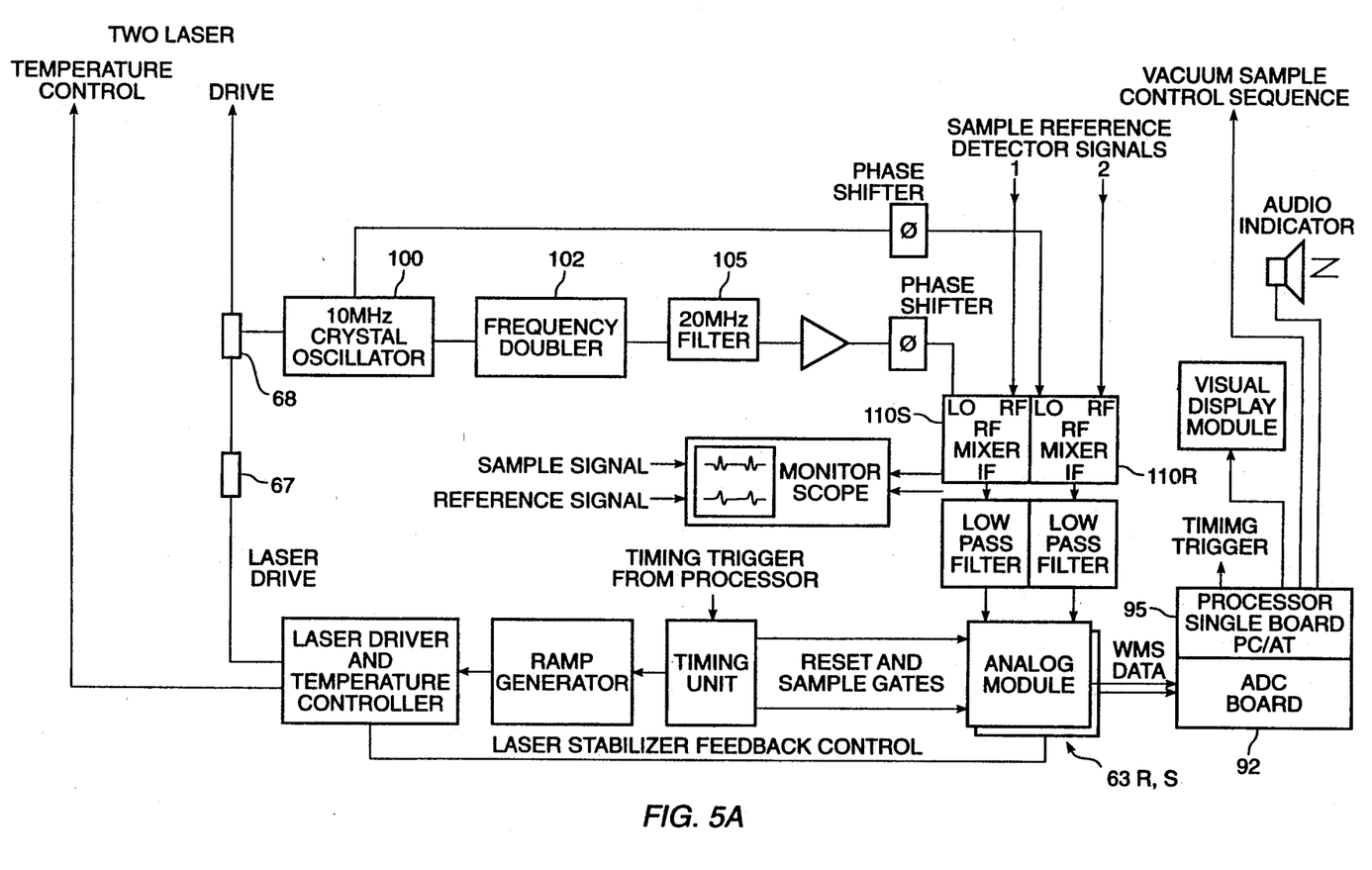
FIGS. 5A–B are block diagrams of wavelength modulation/demodulation circuitry embodiments.

FIG. 5A is a block diagram of control circuitry for an embodiment using a single laser and WMS. This embodiment differs from the embodiment of FIG. 4A in that a different modulation and demodulation regime is used, but the control circuitry and data acquisition circuitry are generally the same. The same reference numerals are used for elements that are the same (e.g., timing unit 60, ramp generator 62, and laser drive circuitry 65).

A crystal oscillator 100 provides a signal at a single modulation frequency; 10 MHz is representative. A portion of the signal is communicated to RF bias network 68 to modulate the laser drive current. As noted above, detection is typically carried out either at the fundamental or the second harmonic. In the case of the single-laser embodiment, there is probably little reason to prefer using the fundamental or the second harmonic. In the particular embodiment illustrated, the reference detector signal is demodulated at the fundamental (10 MHz) while the sample detector signal is demodulated at the second harmonic (20 MHz). Accordingly, a portion of the oscillator signal is passed through a frequency doubler 102 and a band-pass filter 105, while another component is used directly. The 10-MHz and 20-MHz signals are applied to the LO inputs of a pair of mixers 110R and 110S, which receive the detector signals at their respective RF inputs, and provide the demodulated signals at their respective IF outputs. The signals are low-pass filtered and communicated to analog modules 63R and 63S as in the embodiment of FIG. 4A.

Figure 5B:
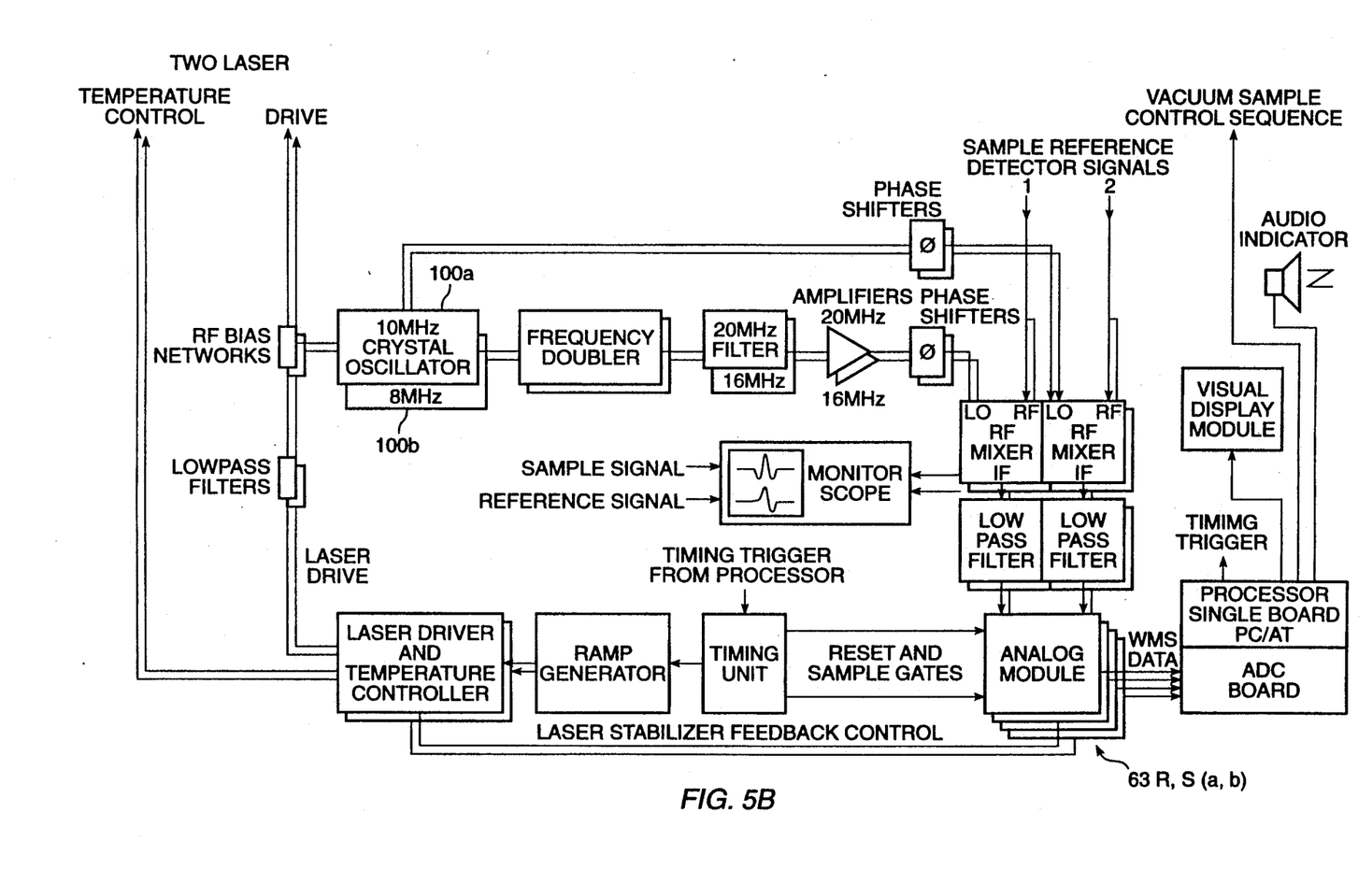

FIG. 5B is a block diagram of control circuitry for an embodiment using two lasers and WMS. As in the case of the embodiment of FIG. 4B, each laser has its wavelength scanned over a range that includes a single one of the two absorption lines. In this embodiment, each laser is modulated at a different frequency, for example 8

MHz and 10 MHz. The circuitry is basically similar to that of a single laser embodiment, except the modulation, demodulation, and laser driver circuits are duplicated so that each detector signal is demodulated at two frequencies. Reference numerals corresponding to those used in FIG. 5A are used, but with the suffixes a and b corresponding to the circuit elements for laser diodes 40a and 40b. In the case where the laser has its wavelength locked to the absorption line, there is a preference to demodulating at least the reference detector signal at the fundamental since the signal has a zero crossing at the absorption line, which makes it easier to servo the laser wavelength.

Experimental Results

According to the AFGL HITRAN data base, the strongest $^{12}CO_2$ transitions in the 1.6-μm spectral region have linestrengths on the order of $2 \times 10^{-23}$ cm and the strongest $^{13}CO_2$ transitions have linestrengths on the order of $2 \times 10^{-25}$ cm. However, the AFGL listings have the relative natural abundances factored into the linestrengths. Hence in computing the absorption coefficients from specific isotopic mixtures of $CO_2$ it is important to divide the AFGL linestrengths by the relative natural abundance. The description below will use only these corrected linestrengths.

A single-mode laser diode operating in the 1.6-μm region (Anritsu Corp.) was mounted on a thermoelectric cooler (Melles Griot Model No. 06DTC003) whose temperature was controlled by a laser diode controller (Melles-Griot Model No. 06DLD003) which also supplied the DC current to the laser. The RF drive to the laser was provided by two RF generators (HP Model Nos. 8350C and 3336B) and it was capacitively coupled to the laser. The modulation frequencies used in most experiments were 335 MHz and 345 MHz, which exceed the 175-MHz Doppler half-width of the $CO_2$ absorptions in this spectral region. The laser wavelength was tuned rapidly over the absorption by ramping the laser current at a 500-Hz rate. The laser output was collimated by a lens assembly coated for 1.55 μm and then directed through a multipass cell of the Herriot design operating in the re-entrant mode. The total volume of the Herriot cell was 2.5 liters, and the total pathlength in the cell was adjusted to 903 cm.

A visible He-Ne laser beam was copropagated with the infrared beam for initial alignment. The output beam from the Herriot cell was focused onto a high-bandwidth InGaAs detector (Mitsubishi PD7002). The RF signal at 10 MHz was filtered and amplified by two amplifiers that provided a total gain of 70 db. The gain was adjusted by variable attenuators. After amplifying and filtering, the signal was directed to the RF port of a double balanced mixer for homodyne detection. The final FM lineshape was again low-pass filtered and then sampled by a digital oscilloscope (Tektronix Model No. 2403A) which was interfaced to an 80386 personal computer for data acquisition.

The laser wavelength was measured with a 0.01-$cm^{-1}$ resolution using a Burleigh Wavemeter (Model No. WA20DL). The laser had a tuning range from 6246 $cm^{-1}$ to 6232 $cm^{-1}$. We concentrated our efforts on two closely spaced absorptions at 6237.43 $cm^{-1}$ and 6237.16 $cm^{-1}$ for $^{12}CO_2$ and $^{13}CO_2$ respectively. These lines are not optimum for this application but we were limited by the tuning range of the laser from reaching the optimum lines. According to the HITRAN database the linestrengths of these absorptions (corrected for the relative natural abundance) are $1.592 \times 10^{-23}$ cm and $8.794 \times 10^{-24}$ cm. These lines were first identified using pure $^{12}CO_2$ and $^{13}CO_2$ before experiments on human breath were carried out. In order to confirm that we were monitoring the correct lines the line positions and strengths of several other $CO_2$ lines in the HITRAN database were identified and measured.

The absorption cross-section, and consequently the TTFMS signal, from any absorbing species is a function of pressure because of collisional broadening. The lines monitored in these experiments had different collisional broadening coefficients (0.074 $cm^{-1}atm^{-1}$ for $^{12}CO_2$ and 0.076 $cm^{-1}atm^{-1}$ for $^{13}CO_2$. We calculated the ratio of the absorption cross section, σ, times the concentration, N, for the $^{12}CO_2$ and $^{13}CO_2$ lines we monitored as a function of pressure, and found that it changes by about 3% over a pressure range of 9-50 torr. Most measurements were done at pressures less than 50 torr for practical reasons. It is easier to modulate a laser diode at relatively low frequencies so it would be desirable if pressure broadening were kept to a minimum and the absorption linewidth remained comparable to the modulation frequency. Also from the point of view of making an instrument for clinical applications, it would be easier if the patient did not have to fill a large volume with relatively high pressure. In our case filling a small balloon with a 0.5-liter breath sample was more than sufficient for filling the multipass cell to a total pressure of 50 torr.

Since the two lines monitored have such different intensities it was necessary to change the gain in the $CO_2$ amplifier chain when scanning over the two absorptions. Thus we had to insure that our system had the necessary dynamic range to detect both lines. In order to calibrate the responsivity and the dynamic range of our system as a function of RF gain and the gas pressure in the cell, several runs were done to confirm the linearity of the signal. The data showed that the our system had a dynamic range of at least 35 db and that the signal remained fairly linear up to 40 to 50 torr.

Figure 6A:
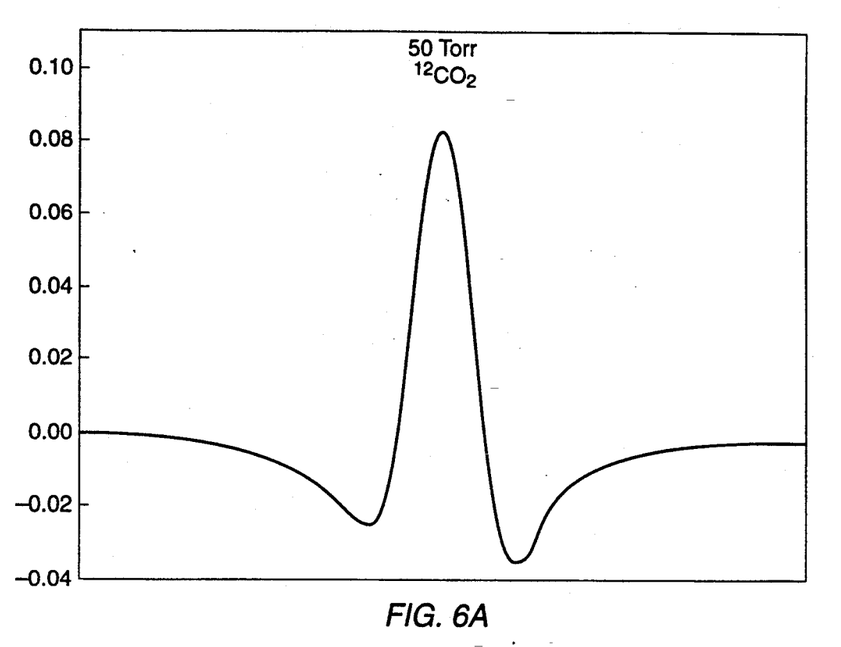
FIGS. 6A–B show wavelength scan signals for particular $^{12}$CO$_2$ and $^{13}$CO$_2$ lines.
Figure 6B:
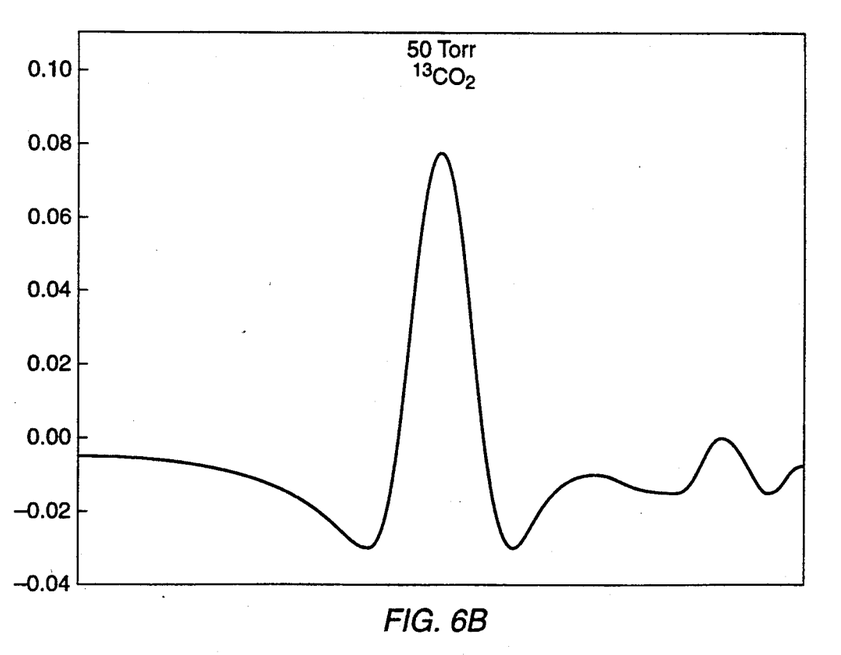

FIG. 6A shows a wavelength scan over the $^{12}CO_2$ absorption at 6237.43 $cm^{-1}$ with 50 torr of breath sample and a total gain of 40 db. Similarly, FIG. 6B shows the signal from the $^{13}CO_2$ absorption at 6237.16 $cm^{-1}$ from the same 50 torr breath sample. The gain in this case was 70 db. The ratio of these two signals accounting for the 30-db gain difference is 168.3. Using the linestrength and pressure broadening coefficient values as listed in the HITRAN database the theoretical ratio of the absorption cross sections for these lines at 50 torr is calculated to be 166.4, slightly lower than the experimental value. The difference may be attributed to small non-linearities in the amplifier chain and inaccuracies in our pressure gauge. This ratio declined by about 3% as the pressure was reduced gradually to 18 torr. In the $^{13}CO_2$ scan another weak line is noticeable towards the end of the scan. We determined that this line is due to $^{12}C^{18}O^{16}O$ at 6237.06 $cm^{-1}$ which has a linestrength of $5.751 \times 10^{-24}$. The signal-to-noise ratios for these scans are well over 100 which allows for a $^{13}CO_2/^{12}CO_2$ ratio measurement precision of greater than 1%. This precision is adequate for medical diagnostic applications since the natural fluctuations of the $^{13}CO_2/^{12}CO_2$ ratio on human breath are on the order of 1%. The sensitivity of our system was calibrated using both pure $^{12}CO_2$, pure $^{13}CO_2$, and breath samples. Our apparatus was generally capable of measuring absorptions as small as $1 \times 10^{-6}$. No effort was made to subtract RAM, etalon fringes, or laser excess noise. The sensitivity can probably be improved by using a noise subtraction scheme and also by using a Faraday isolator to reduce the effects of optical feedback into the laser.

Although these lines were only 0.27 cm$^{-1}$ apart, the fact that substantially different gains were required for the two lines made a single scan measurement impossible using a specific amplifier gain. Although it is possible to monitor each line with a separate laser diode, it is generally preferable to use a single laser for both lines. This requires a set of lines whose intensities are more nearly matched and whose wavelengths are more closely spaced. There are several sets of absorptions that fulfill these requirements. For example a $^{12}CO_2$ line at 6228.6938 cm$^{-1}$ and a $^{13}CO_2$ line at 6228.4370 cm$^{-1}$ are much better lines to monitor. The ratio of their absorption cross sections at 50 torr is 10.4, so a much smaller dynamic range for the RF electronics is adequate. Due to the limited tunability of our laser, we could not access these absorptions, but a different laser diode could monitor these lines simultaneously with adequate precision.

Portable Instrument

Figure 7:
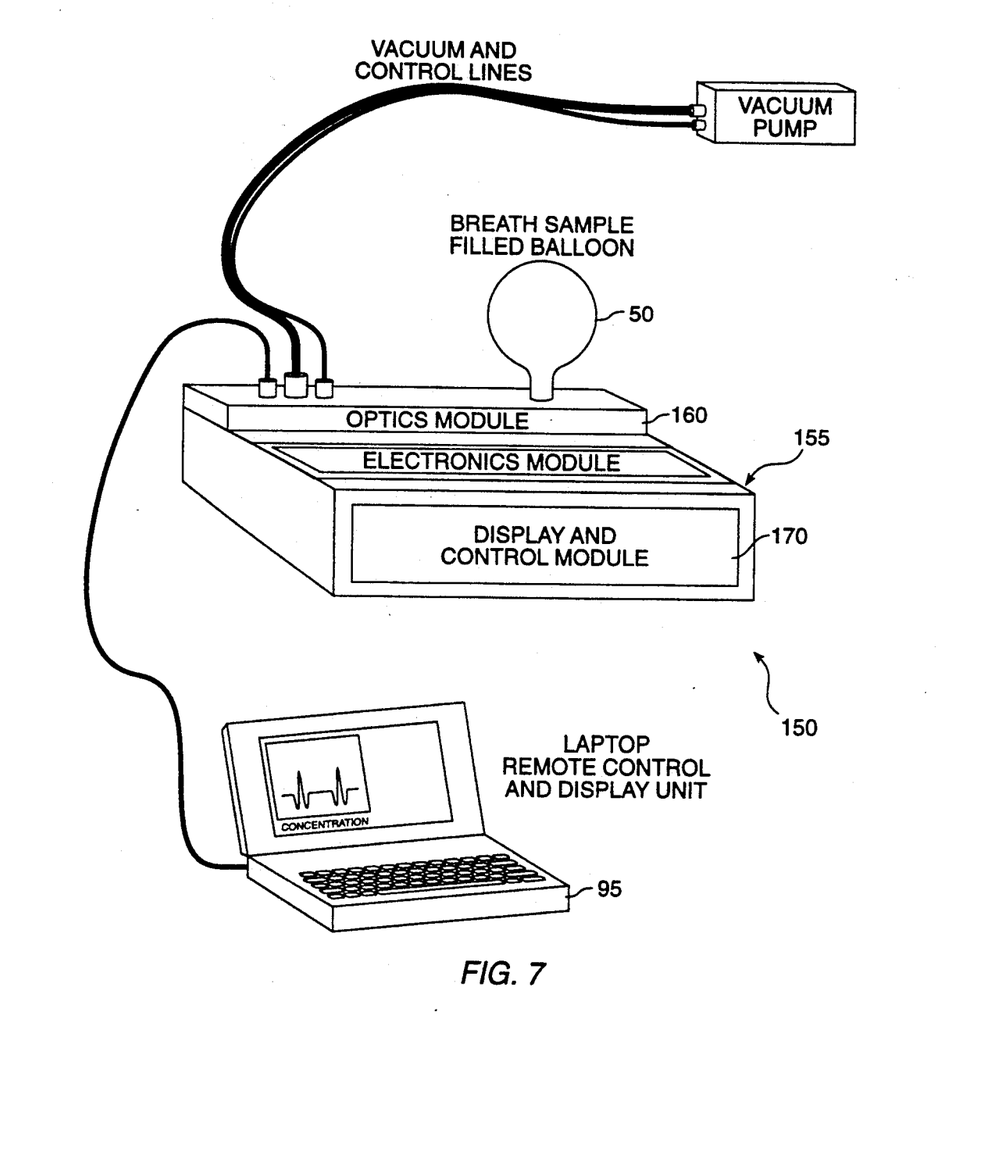
FIG. 7 shows a portable instrument embodying the present invention.

FIG. 7 is a perspective rendition of an instrument 150 embodying the present invention. The instrument includes a main housing 155 containing an optics module 160 that incorporates laser illumination subsystem 15, cells 12R and 12S, and detectors 20R and 20S, and electronics and control modules 20S, 165 and 170 that include drive and modulation circuitry 30. Microcomputer 95 is preferably implemented as a laptop device connected to the main housing via a cable.

Conclusion

In summary, it can be seen that the present invention provides a relatively inexpensive and safe technique for performing a number of medical tests. The use of room-temperature laser diodes avoids the need for bulky and costly cryogenic equipment and permits apparatus for performing such tests to be implemented in a compact portable instrument.

While the above is a complete description of specific embodiments, alternative constructions, modifications, and equivalents may be used. For example, the specific absorption lines discussed above are in the 1.6-$\mu$m wavelength range, which can be measured with presently commercially available room-temperature laser diodes. However, researchers are currently working on room-temperature devices that operate in the 2-$\mu$m to 3-$\mu$m range, and such devices would be suitable. A possible pair of absorption lines using such a device would be the $^{12}CO_2$ absorption at 4870.436 cm$^{-1}$ and the $^{13}CO_2$ absorption at 4870.4917 cm$^{-1}$. Furthermore, operation in this wavelength region would allow the technique to be extended to isotopic species of other compounds such as carbon monoxide and methane.

Therefore, the above description and illustration should not be taken as limiting the scope of the invention which is defined by the claims.

What is claimed is:

1. Apparatus for determining information regarding the presence of first and second isotopic species in a molecular gas sample comprising:
    a sample cell for holding the gas sample to be analyzed;
    a reference cell for holding a volume of gas having a known ratio of the first and second isotopic species;
    a laser diode illuminator for passing light of first and second wavelengths in the 1-$\mu$m to 3-$\mu$m range through both said sample cell and said reference cell;
    said first wavelength being at an absorption line for molecules containing said first isotopic species;
    said second wavelength being at an absorption line for molecules containing said second isotopic species;
    means for modulating the light at each of said first and second wavelengths according to a particular regime;
    means for demodulating the light at each of said first and second wavelengths according to said particular regime to provide respective signals corresponding to the absorption at each of said first and second wavelengths in each of said sample and reference cells; and
    means for correlating said respective signals to provide a representation of the isotope ratio in said sample cell.

2. Apparatus for determining information regarding the presence of first and second isotopic species in a molecular gas sample comprising:
    a sample cell for holding the gas sample to be analyzed;
    a reference cell for holding a volume of gas having a known ratio of the first and second isotopic species;
    a laser diode illuminator for passing light of first and second wavelengths through both said sample cell and said reference cell, said laser diode illuminator having a normal operating temperature that is in the range of approximately 0°-50° C.;
    said first wavelength being at an absorption line for molecules containing said first isotopic species;
    said second wavelength being at an absorption line for molecules containing said second isotopic species;
    means for modulating the light at each of said first and second wavelengths according to a particular regime;
    means for demodulating the light at each of said first and second wavelengths according to said particular regime to provide respective signals corresponding to the absorption at each of said first and second wavelengths in each of said sample and reference cells; and
    means for correlating said respective signals to provide a representation of the isotope ratio in said sample cell.

3. The apparatus of claim 1 or 2 wherein said illuminator comprises:
    a single laser diode; and
    means for changing at least one operating characteristic of said laser diode to change the laser wavelength over a range that includes said first and second wavelengths.

4. The apparatus of claim 1 or 2 wherein said illuminator comprises:
    first and second laser diodes operating at said first and second wavelengths, respectively.

5. The apparatus of claim 1 or 2 wherein:
    said means for modulating comprises means for modulating the light of a given optical frequency at first and second RF modulation frequencies to produce multiple sidebands displaced from the optical frequency by integral multiples of said first and second modulation frequencies; and said means for demodulating comprises means for detecting a signal at a specific integral multiple of the difference between said first and second modulation frequencies.

6. The apparatus of claim 5 wherein said specific integral multiple of the difference is the difference itself.

7. The apparatus of claim 1 wherein:
said means for modulating comprises means for modulating the light of a given optical frequency at a single RF modulation frequency to produce multiple sidebands displaced from the optical frequency by integral multiples of said single modulation frequency; and said means for demodulating comprises means for detecting a signal at an integral multiple of the single modulation frequency.

* * * * *